United States Patent
Schembri

[11] Patent Number: 6,162,400
[45] Date of Patent: Dec. 19, 2000

[54] APPARATUS FOR CONTROLLING REACTIONS

[75] Inventor: Carol T. Schembri, San Mateo, Calif.

[73] Assignee: Agilent Technologies, Inc., Palo Alto, Calif.

[21] Appl. No.: 09/133,102

[22] Filed: Aug. 12, 1998

[51] Int. Cl.[7] .................................................. G01N 1/10
[52] U.S. Cl. ............................ 422/72; 422/100; 422/103
[58] Field of Search .............................. 422/63, 72, 100, 422/103; 436/45, 174, 180; 137/53, 57

[56] References Cited

U.S. PATENT DOCUMENTS

| | | | |
|---|---|---|---|
| 3,225,778 | 12/1965 | Londal | 137/54 |
| 3,265,081 | 8/1966 | Stockton et al. | 137/54 |
| 3,899,296 | 8/1975 | Mailen et al. | 422/72 |
| 3,945,928 | 3/1976 | Ayres | 210/83 |
| 4,585,558 | 4/1986 | Rubin | 210/360.1 |
| 4,857,274 | 8/1989 | Simon | 422/72 |
| 4,865,810 | 9/1989 | Simon | 422/72 |
| 4,880,731 | 11/1989 | Kaspar | 435/7 |
| 4,894,204 | 1/1990 | Cornut | 422/72 |
| 5,039,401 | 8/1991 | Columbus et al. | 210/117 |
| 5,089,417 | 2/1992 | Wogoman | 436/45 |
| 5,171,533 | 12/1992 | Fine et al. | 422/72 |
| 5,173,193 | 12/1992 | Schembri | 210/782 |
| 5,242,606 | 9/1993 | Braynin | 210/787 |
| 5,398,713 | 3/1995 | Whitman | 137/54 |
| 5,627,041 | 5/1997 | Shartle | 435/7.24 |
| 6,013,513 | 1/2000 | Reber et al. | 435/288.5 |

FOREIGN PATENT DOCUMENTS

0417305  12/1991  European Pat. Off. .

*Primary Examiner*—Jeffrey Snay
*Attorney, Agent, or Firm*—Trueman H. Denny, III; Gordon Stewart

[57] ABSTRACT

The invention relates to a method and an apparatus for performing an assay on chemical, biochemical, or biological fluids. The apparatus includes an assay chamber for fluid reactions and a centrifugal force activated-valve for controlling fluid movement through the assay chamber. An active surface can be positioned in the assay chamber to react with fluids passed through the assay chamber. The active surface may contain biomolecular probes. The biomolecular probes can be DNA, DNA fragments, RNA, RNA fragments, reagents, protein, protein fragments, lipids, and lipid fragments. The apparatus is particularly useful when multiple reactions, dilutions, or washing steps are required to determine a final answer. The centrifugal force activated-valve provides positive control over fluid in the assay chamber and allows for repeated use of the same chamber for multiple reaction steps. The apparatus can be disposed of after an assay to eliminate potential contamination from reuse of the same apparatus. Fluids passed through the assay chamber may be recovered for subsequent analysis, processing, or reactions.

23 Claims, 6 Drawing Sheets

APPARATUS FOR CONTROLLING REACTIONS

BACKGROUND OF THE INVENTION

The present invention relates generally to analytical devices for performing assays and more particularly to an analytical device that includes a centrifugal force actuated valve to control fluid and a method of utilizing the analytical device to perform an assay.

There are many analytical methods that require one or more reactions or analytical steps to determine a final answer. Examples are heterogeneous immunochemistry reactions, hybridization of DNA to DNA, and hybridization of DNA to RNA. In order to determine the concentration or presence of an analyte, such analytical methods require multiple, serial reactions either with or without washing steps or a single reaction with a washing step. Other assays, such as clinical chemistry assays, often require precise dilutions prior to mixing with other chemicals.

It would be desirable to reduce the cost of conducting the reactions in an assay by automating the reaction steps rather than using expensive manual labor to perform the steps. Additionally, it would be advantageous to use centrifugal force in the automation process to minimize variations due to surface tension and capillary action and to move and control fluid.

Centrifugally driven analytical devices have employed several methods for controlling fluid movement, such as differential flow, stop junctions, siphons, and complex, two-axis mechanisms.

Differential flow allows fluid to enter a chamber quickly but exit slowly. As the fluid enters and exits the chamber there is a finite residence time in which most of the fluid can be manipulated. However, the disadvantage of differential flow is that the entire volume of fluid is never completely controlled.

Stop junctions employ the pressure created by a capillary to stand off fluid flow until the centrifugal force generated by rotation overcomes capillary back pressure. Stop junctions are sensitive to the exact geometry and surface properties of the junction and to fluid properties of the sample.

Siphons allow fluid movement into a chamber under the action of centrifugal force and prevent the fluid from exiting the chamber until the siphon is primed or the siphon level is high enough. The disadvantage with siphons is that some of the fluid is lost in the entrance of the siphon and that great care must be taken to prevent the siphon from priming prematurely or from losing prime prematurely.

Two-axis mechanisms provide better fluid control, but at substantial instrumentation cost, complexity, and size. Two-axis mechanisms are typically mounted on a large turntable. The turntable has two positions, each position having a local center of rotation.

U.S. Pat. No. 5,171,533 to Fine et al. discloses single use centrifugal valves for performing a biological assay. Sealant materials are used to provide a counteracting force to the centrifugal force of rotation. The sealants are designed to yield at predetermined levels of centrifugal force. The valves in the Fine et al. patent require that the fluid move through different chambers.

From the foregoing it will be apparent that there is a need for a simple, easy to automate, and economical means for performing an assay or a reaction. Further, it will be apparent that a disposable analytical device is desirable for preventing contamination resulting from repeated use of the same analytical device.

SUMMARY OF THE INVENTION

The invention provides an analytical device incorporating a centrifugal force-activated valve for controlling reactions and for moving fluid within the analytical device. The centrifugal force-activated valve allows for several fluids to be passed through the analytical device and allows the analytical device to be used for multiple serial reactions. The centrifugal force-activated valve provides simple and reliable control over fluid movement and can be tuned to open or close over a wide range of rotational speeds.

An analytical device embodying the invention is economical, easy to use, injection moldable from a variety of plastics, readily adaptable to automation, capable of repeated reaction, mixing, and washing steps, disposable to prevent contamination, and may be transparent to allow an assay by optical detection means.

In a preferred embodiment of an analytical device, according to the present invention, a housing enclosure adapted for rotation about an axis includes an assay chamber, a fluid discharge port in fluid communication with the assay chamber, means for introducing fluid into the assay chamber, and a centrifugal force-activated valve in fluid communication with the fluid discharge port. Preferably, the fluid introducing means is self sealing. Fluid entering the valve through the fluid discharge port may exit the valve through a fluid drain. The fluid drain is in fluid communication with the valve and an exterior portion of the housing enclosure. Chemical, biological, or biochemical fluids may be introduced into the assay chamber.

Additionally, an active surface can be positioned on an interior surface of the assay chamber. The active surface may contain biomolecular probes. The biomolecular probes can be DNA, DNA fragments, RNA, RNA fragments, reagents, protein, protein fragments, lipids, and lipid fragments. Additionally, the active surface can be disposed on a structure positioned on an interior surface of the assay chamber. For example, the structure can be in the shape of balls or beads. The structure can be attached to an interior surface of the assay chamber or can be loosely contained in the assay chamber. Typically, the active surface is arranged in an array pattern positioned on a surface of the assay chamber.

An analytical substrate can be positioned in an opening in the housing enclosure. The active surface can be disposed on an interior surface of the analytical substrate and in opposing relation to the assay chamber.

The analytical substrate can be made transparent, to optical detection means external to the housing enclosure. A transparent analytical substrate allows for an assay of the active surface by scanning the active surface through the analytical substrate using the optical detection means.

The analytical device may also include a reservoir chamber disposed radially outward from the centrifugal valve and in fluid communication with the valve. Fluid exiting the centrifugal valve is stored in the reservoir chamber. Optionally, fluid contained in the reservoir chamber can be extracted through fluid extracting means in fluid communication with the reservoir chamber. Preferably, the fluid extraction means is self sealing.

In another embodiment, the housing enclosure includes a portion defining a valve chamber for containing the centrifugal force-activated valve. A fluid discharge port is positioned at a radially inward end of the valve chamber and is in fluid communication with the valve chamber and the assay chamber. A valve seat is disposed in the valve chamber and is disposed radially outward from the fluid discharge port. The valve seat is in fluid communication with the fluid discharge port and the valve chamber. An actuator is movably disposed in the valve chamber and is biased to a stationary position relative to the valve seat by a counter, acting force provided by bias means positioned in the valve chamber and disposed radially outward from the actuator. The actuator moves radially outward from the stationary position to an actuated position when the housing enclosure is rotated and the centrifugal force acting on the actuator exceeds the counteracting force of the bias means. When the centrifugal force drops below the counteracting force, the actuator moves radially inward from the actuated position to the stationary position.

A method according to the present invention includes injecting a sample into the assay chamber through the fluid introducing means. The analytical device is then spun at a first rotational speed lower than that required to actuate the centrifugal force-activated valve. The first rotational speed needs to be sufficient to distribute the sample across the active surface. The sample is allowed to react with the active surface. At the conclusion of the reaction period, the analytical device is spun at a second rotational speed to actuate the centrifugal force-activated valve and empty the sample from the assay chamber. Spinning at the second rotational speed is stopped when the assay chamber is empty. Wash fluids are injected into the assay chamber and the analytical device is spun at the first rotational speed to distribute the wash fluids. The analytical device is then spun at the second rotational speed to empty the wash fluids. The washing step can be repeated as necessary to effect complete washing of the assay chamber and the active surface. After the washing step, the active surface can be scanned to detect the presence of an analyte.

Other aspects and advantages of the present invention will become apparent from the following detailed description, taken in conjunction with the accompanying drawings, illustrating by way of example the principles of the invention.

DETAILED DESCRIPTION

In the following detailed description and in the several figures of the drawings, like elements are identified with like reference numerals.

As shown in the drawings for purposes of illustration, the invention is embodied in an analytical device having an assay chamber for fluid reactions and at least one centrifugal force-activated valve in fluid communication with the assay chamber. The valve provides positive control of fluid contained in the assay chamber and allows for multiple, fluid reaction steps, mixing steps, and washing steps to occur in the assay chamber. The analytical device of the present invention is easy to use, can be manufactured at low cost, is adaptable to automation, provides predictable fluid control that can be tuned over a wide range of rotational speeds, and can be disposed of after use to prevent contamination from repeated use of the same analytical device. Previous apparatus for controlling reactions have incorporated complex fluid control methods, such as, siphons, stop junctions, two-axis rotation, differential flow, and single use centrifugal valves. The analytical device of the present invention provides positive fluid control with less complexity and greater flexibility than the previous apparatus.

Figure 1:
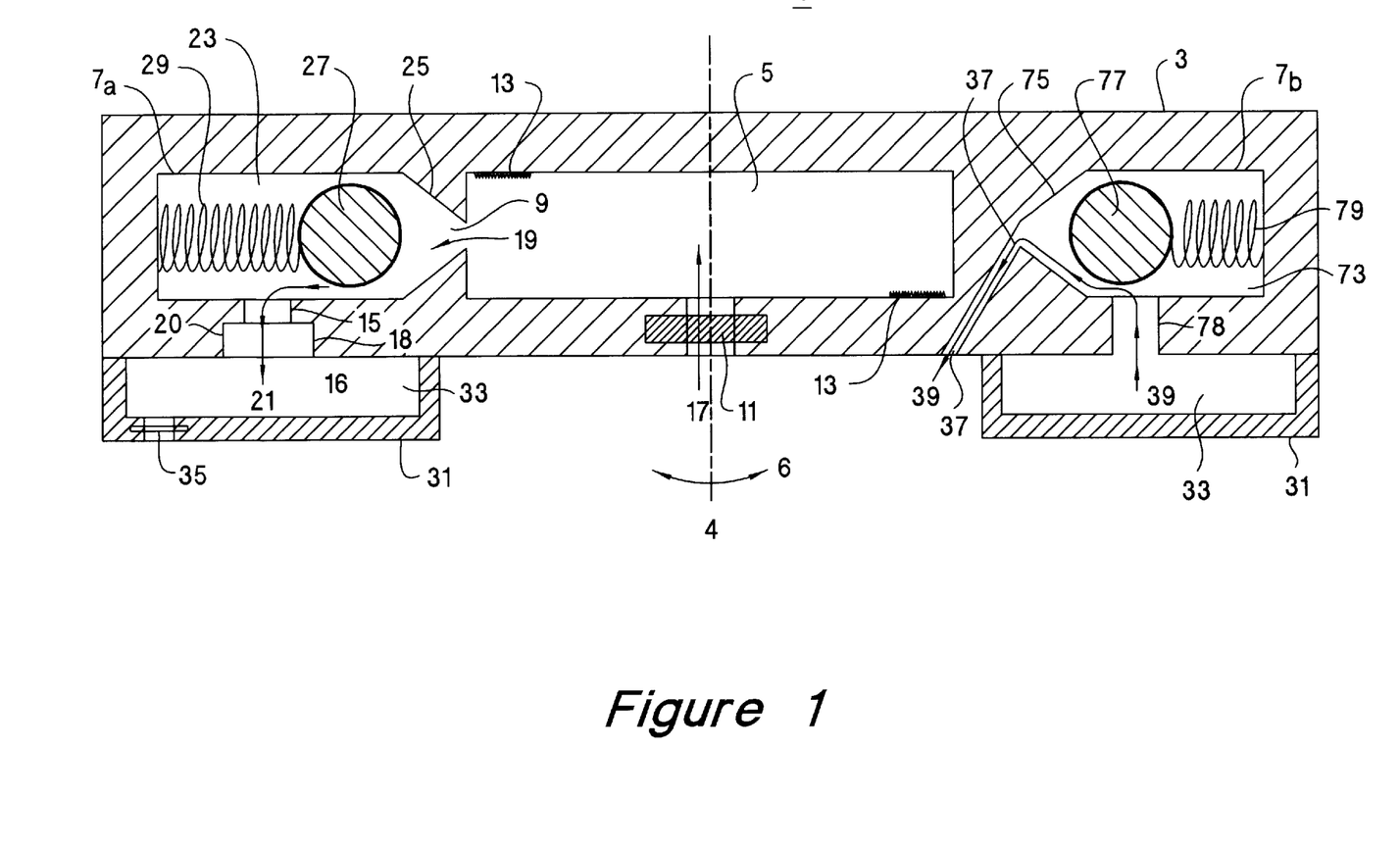
FIG. 1 is a cross section of an analytical device according to the present invention.

Referring to FIG. 1, there is provided in accordance with the present invention an analytical device generally designated as 1. The analytical device includes a housing enclosure 3 defining an assay chamber 5, and a centrifugal force-activated valve 7a disposed radially outward of the assay chamber 5. The housing enclosure 3 is adapted for rotation 6 about a rotational axis 4. Fluid is communicated from the assay chamber 5 to the valve 7a, as shown by arrow 19, thru a fluid discharge port 9 positioned intermediate to the assay chamber 5 and the valve 7a. An active surface 13 can be positioned on an interior surface of the assay chamber 5. Fluid is introduced into the assay chamber 5, as shown by arrow 17, using fluid introducing means 11. Fluid introducing means 11 is in fluid communication with the assay chamber 5. Fluid introducing means 11 can be an opening positioned in the housing enclosure 3 near the rotational axis 4. Preferably, fluid introducing means 11 is self sealing, for example, a diaphragm or a septum. If the reaction is fast or the volumes of fluid large enough that evaporation is not an issue, the fluid introducing means 11 need not be sealed. Rotation 6 of the housing enclosure 3 generates a radially outward flow of fluid contained in the assay chamber 5, thereby urging the fluid into contact with the fluid discharge port 9. Additionally, it is desirable to position the active surface 13 at a radially outward portion of the assay chamber 5 to allow fluid to react with the active surface 13 when the housing enclosure 3 is rotated and the fluid is urged radially outward. When the centrifugal force from rotation 6 of the housing enclosure exceeds the force necessary to actuate the valve 7a, the valve opens, and fluid enters the valve 7a through the fluid discharge port 9. In a typical application, chemical, biochemical, or biological fluids are reacted in the assay chamber.

The centrifugal force-activated valve 7a, includes a valve chamber 23, a valve seat 25 positioned radially outward of the fluid discharge port 9, an actuator 27 movably positioned in the valve chamber 23, and bias means 29 positioned in the valve chamber 23 and radially outward of the actuator 27. The bias means 29 provides a counteracting force to urge the actuator 27 into a stationary position relative to the valve seat 25. As will be further described below with respects to FIGS. 3a, 3b, 4a, and 4b, the valve seat may be positioned radially inward or radially outward of the actuator. Additionally, a fluid drain 15 can be positioned in the valve chamber 23. The fluid drain 15 allows fluid entering the valve chamber 23 as shown by arrow 19, to exit the valve 7a through the exterior of the housing enclosure 3, as shown by arrow 21.

In a typical embodiment of the present invention, housing enclosure 3 can be made from almost any structural material. Obvious choices include metals, ceramics, plastics, fused silica, and glasses. The housing enclosure 3 can be machined from metal, for example, steel, aluminum, and copper. The housing enclosure 3 can also be machined or injection molded from plastic. Stainless steel is a preferred metal since it won't generally react with the chemical analysis occurring in the analytical device 1. More preferred, especially for a disposable analytical device, is injection molded plastics. Possible choices for injection molded plastics include acrylic (polymethyl methacrylate), polyethylene, polypropylene, polystyrene, ABS, polycarbonate, and the like. Selection of the material for the housing enclosure 3 is dependent on the specific requirements for the assay. For example, polypropylene is desirable because of its higher temperature limits and inertness; however, the inertness of polypropylene make it difficult to label and difficult to glue in subsequent manufacturing assembly steps. Typically, the valve chamber 23 and the valve seat 25 are made of the same material as the housing enclosure 3.

The actuator 27 can also be made of the same materials as the housing enclosure 3. Preferably, the actuator 27 is made from a dense, inert material, such as, a stainless steel ball. Stainless steel balls are easily obtained and the material is dense and inert. The shape and material properties of the actuator 27 should be compatible with motion of the actuator 27 in the valve chamber 23. Actuator 27 should move back and forth in the valve chamber 23 with minimal friction, and should be properly shaped and sized to prevent binding in the valve chamber 23. Suitable shapes for actuator 27 include a ball, a machined shape, and a molded shape.

Referring to FIG. 1, bias means 29 provides a counteracting force to urge the actuator 27 to a stationary position relative to the valve seat 25. Rotation 6 of the housing enclosure 3 generates centrifugal forces that urge the actuator 27 to move radially outward in opposition to the counteracting force of bias means 29. The magnitude of the centrifugal force acting on actuator 27 is proportional to the product of the mass of the actuator 27 and the square of the rotational velocity of the housing enclosure 3 divided by the radial distance of the actuator 27 from the rotational axis 4. The counteracting force of bias means 29 can be provided by a compression spring, a compressible material, a coil spring, a leaf spring, or a diaphragm. For purposes of illustration, FIG. 1 shows a coil spring. The centrifugal force-activated valve of the present invention can be tuned to actuate at a predetermined rotational speed by selecting the mass of the actuator 27 and the counteracting force of bias means 29.

In a preferred embodiment of the present invention, valve seat 25 is integral to the valve chamber 23 and is made of the same material as the housing enclosure 3. Valve seat 25 operates to prevent fluid communication between the fluid discharge port 9 and the valve chamber 23 when the actuator 27 is forcefully engaged with the valve seat 25. Centrifugal force-activated valve 7a operates as a normally closed valve when the valve seat 25 is positioned radially inward of the actuator 27. For a normally open valve, valve seat 25 is positioned radially outward of the actuator 27.

Figure 3A:
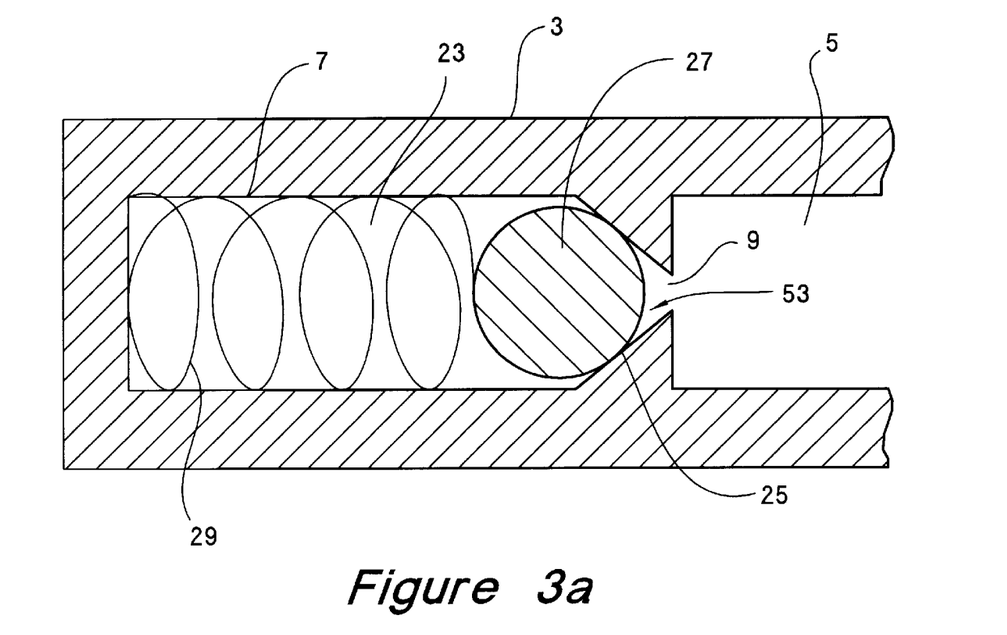
FIG. 3a is a cross section of a normally closed centrifugal force-activated valve in the stationary position according to the present invention.
Figure 3B:
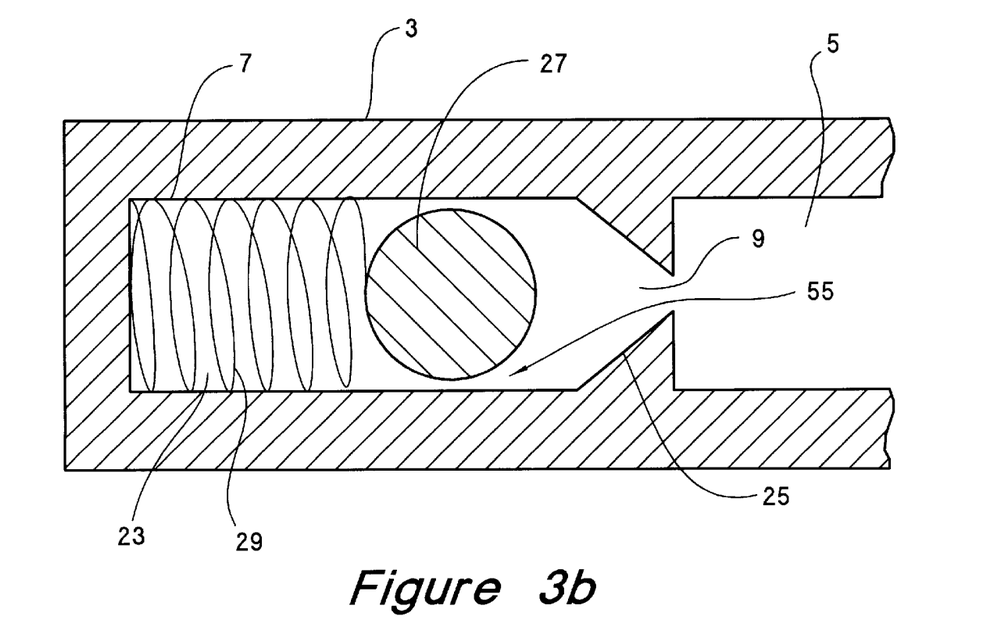
FIG. 3b is a cross section of a normally closed centrifugal force-activated valve in the actuated position according to the present invention.

Referring to FIGS. 3a and 3b, there is provided an illustration of a normally closed centrifugal force-activated valve 7 according to the present invention. FIG. 3a shows actuator 27 biased into a stationary position by bias means 29. In the stationary position, actuator 27 is forcefully engaged with the valve seat 25 and fluid communication between the fluid discharge port 9 and the valve chamber 23 is prevented, as shown, by arrow 53. Actuator 27, moves radially outward from the stationary position to an actuated position when the housing enclosure 3 is rotated and the centrifugal force acting on actuator 27 exceeds the counteracting force of bias means 29. In the actuated position, as shown in FIG. 3b, actuator 27 is disengaged from valve seat 25 allowing fluid communication between the fluid discharge port 9 and the valve chamber 23, as shown by arrow 55.

Figure 4A:
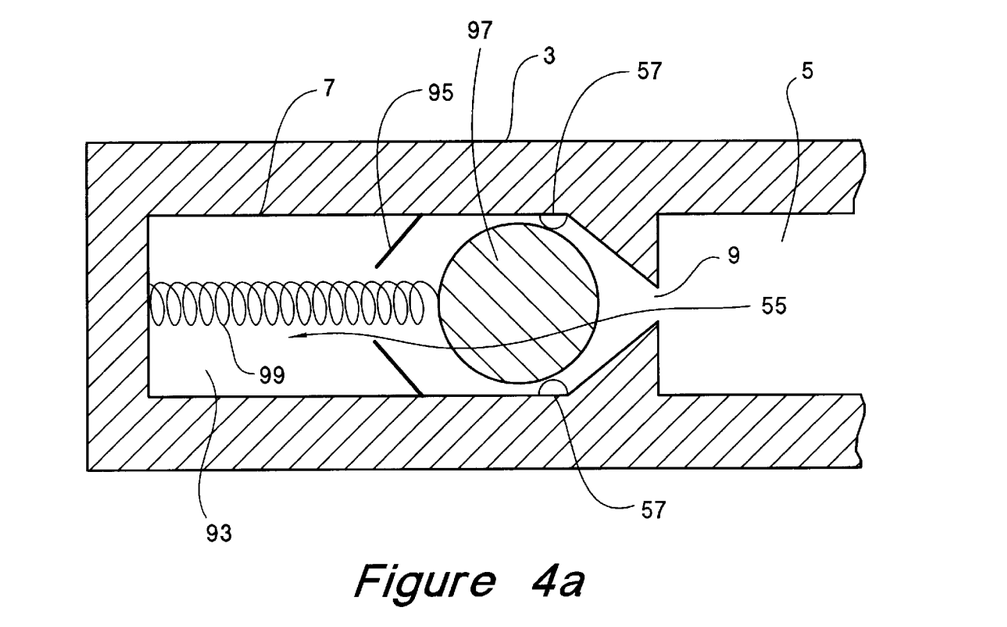
FIG. 4a is a cross section of a normally open centrifugal force-activated valve in the stationary position according to the present invention.
Figure 4B:
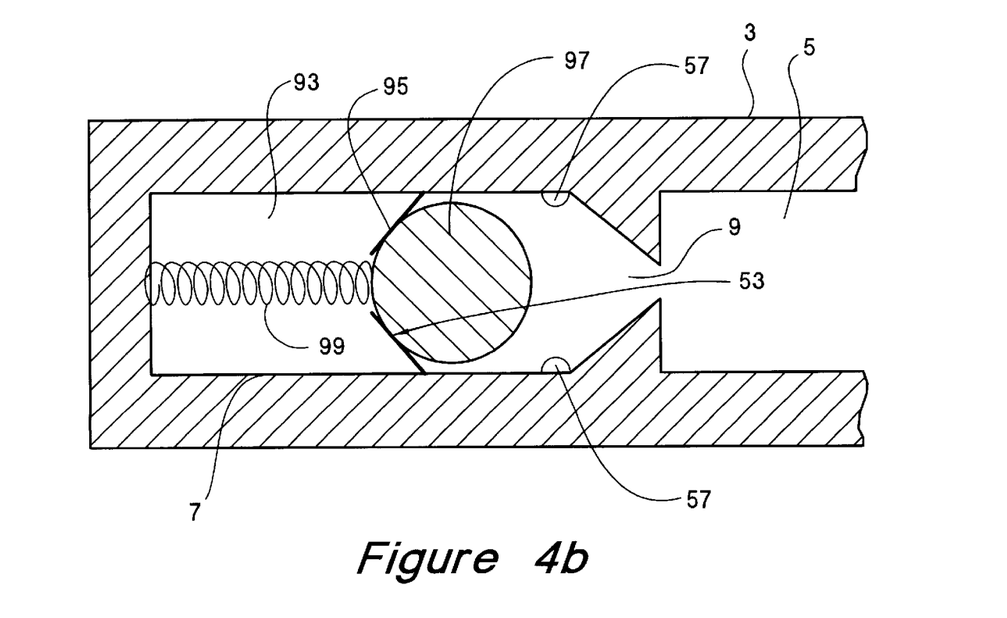
FIG. 4b is a cross section of a normally open centrifugal force-activated valve in the actuated position according to the present invention.

Referring to FIGS. 4a and 4b, there is provided an illustration of a normally open centrifugal force-activated valve 7 according to the present invention. FIG. 4a shows actuator 97 biased into a stationary position by bias means 99. In the stationary position, actuator 97 is forcefully disengaged from the valve seat 95 allowing fluid communication between the fluid discharge port 9 and the valve chamber 93, as shown, by arrow 55. Actuator 97 moves radially outward from the stationary position to an actuated position when the housing enclosure 3 is rotated and the centrifugal force acting on actuator 97 exceeds the counteracting force of bias means 99. In the actuated position, as shown in FIG. 4b, actuator 97 is forcefully engaged with the valve seat 95 preventing fluid communication between the fluid discharge port 9 and the valve chamber 93, as shown by arrow 53. Optionally, it may be desirable to position actuator stops 57 in valve chamber 93 to prevent bias means 99 from urging the actuator 97 into a fluid discharge port 9 blocking position when the actuator is in the stationary position. The actuator stops 57 are disposed radially inward of the actuator 97.

Figure 5A:
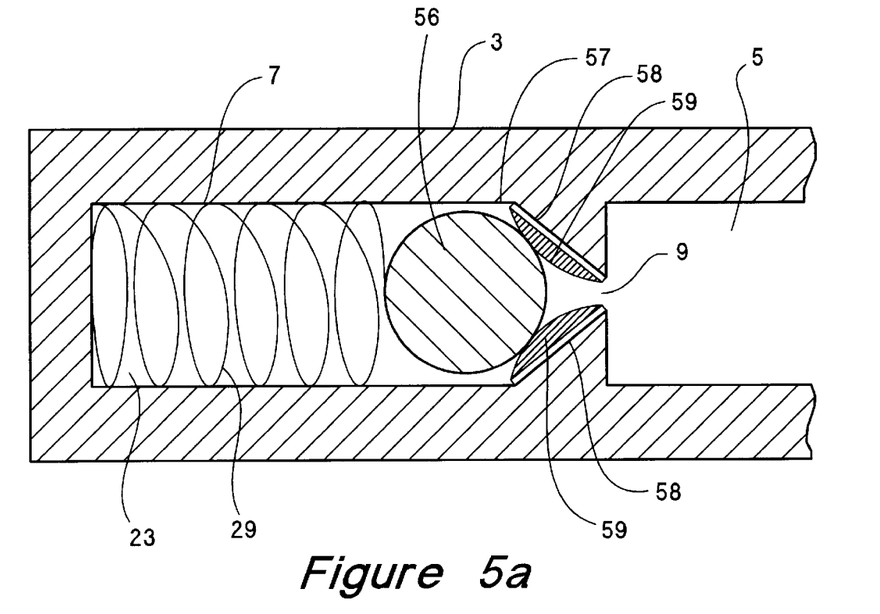
FIG. 5a is a cross section of a valve seat with compliant material according to the present invention.

In another embodiment of the present invention, a compliant material 59 is conformally disposed on the valve seat 58, as illustrated in FIG. 5a. The compliant material 59 forms a tight seal between the actuator 56 and the valve seat 58 when the actuator 56 is forcefully engaged with the valve seat 58. Alternatively, the valve seat 58 may be a compliant material positioned in the valve chamber, for example, an O-ring or a gasket.

Figure 5B:
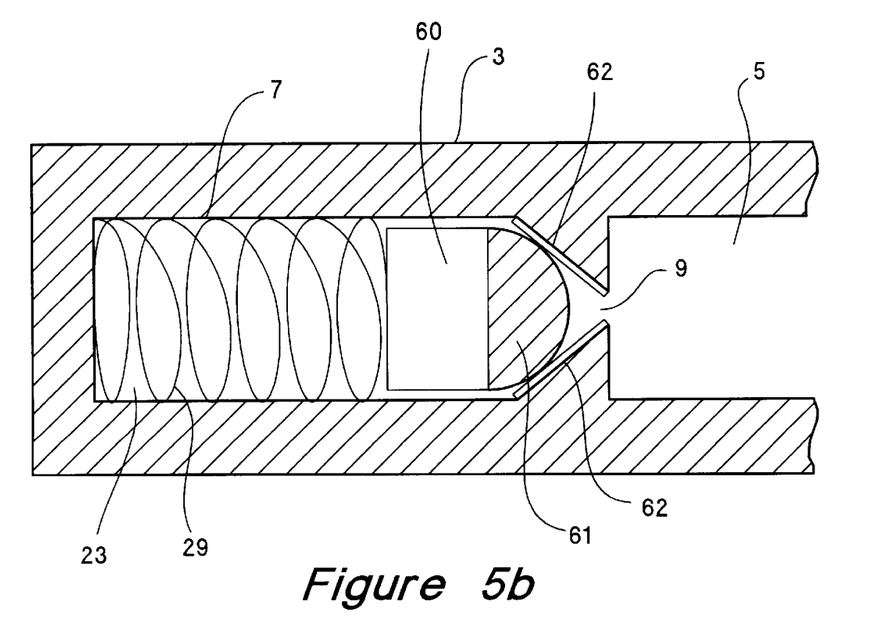
FIG. 5b is a cross section of an actuator with elastomeric material according to the present invention.

Referring to FIG. 5b, in an alternative embodiment of the present invention, an elastomeric material 61 is disposed on the actuator 60. The elastomeric material 61 forms a tight seal between the actuator 60 and the valve seat 62 when the actuator 60 is forcefully engaged against the valve seat 62, preventing fluid communication between the fluid discharge port 9 and the valve chamber 23.

Figures 2A, 2B, 2C:
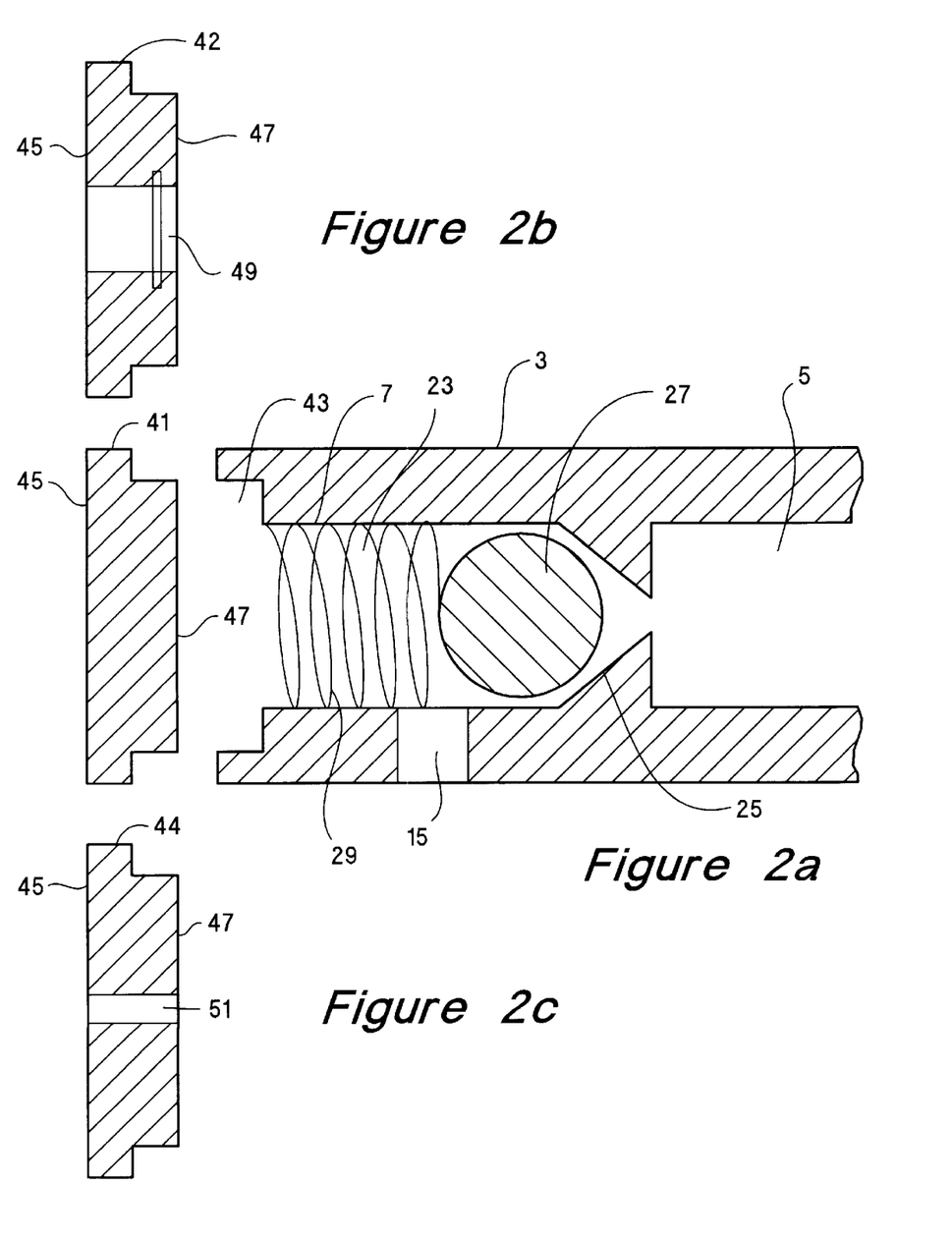
FIG. 2a is a cross section of a centrifugal force-activated valve with a valve chamber cap according to the present invention.
FIG. 2b is a cross section of a centrifugal force-activated valve with a valve chamber cap having fluid extraction means according to the present invention.
FIG. 2c is a cross section of a centrifugal force-activated valve with a valve chamber cap having a fluid drain according to the present invention.

In another embodiment of the present invention, the valve chamber 23 includes a valve chamber cap 41 disposed in valve chamber opening 43, as shown in FIG. 2a. The valve chamber opening 43 is disposed radially outward of the valve chamber 23 and is in fluid communication with the valve chamber 23. The valve chamber cap 41 has an outer surface 45, and an inner surface 47. The inner surface 47 is in fluid communication with the valve chamber 23. The valve chamber cap 41 allows for the insertion of the actuator 27, the bias means 29, and optionally the valve seat 25 into the valve chamber 23. The valve chamber cap 41 can be permanently attached to the valve chamber opening 43, by gluing, welding, fasteners, or the like. The valve chamber cap 41 and the valve chamber opening 43 can be adapted to permit the valve chamber cap 41 to be removably attached to the valve chamber opening 43, for example, using threads, bayonet mount, friction fit, or an o-ring.

One advantage of the removable valve chamber cap 41 is that it allows for application specific selection of a bias means and an actuator. For example, prior to performing an assay using the analytical device 1, a user can select the mass of actuator 27 and the counteracting force of bias means 29 to actuate the centrifugal force-activated valve 7 at a predetermined rotational speed.

In another embodiment of the present invention, as illustrated in FIG. 2b, a valve chamber cap 42 includes fluid extraction means 49 contained in the valve chamber cap 42. Preferably, the fluid extraction means 49 is self sealing, for example, a diaphragm or a septum. The fluid extraction means 49 is in fluid communication with the inner surface 47 and outer surface 45 of the valve chamber cap 42. In some assays, it may be desirable to analyze fluids that have been passed through the assay chamber 5. To extract fluid from the valve chamber 23, a device such as a syringe is inserted through the fluid extraction means 49 to withdraw fluid remaining in the valve chamber 23. Optionally, a radially outward portion of the valve chamber 23 can be sized to capture a specific volume of fluid to be extracted from the valve chamber 23.

FIG. 2c illustrates another embodiment of the present invention. A fluid drain 51 is disposed in a valve chamber cap 44. Fluid drain 51 is in fluid communication with the inner surface 47 and the outer surface 45 of the valve chamber cap 44. Fluid entering the valve chamber 23 exits the valve chamber 23 through the fluid drain 51. Fluid drain 51 in valve chamber cap 44 may either supplement or replace fluid drain 15 in the valve chamber 23.

In an alternative embodiment of the present invention, as illustrated in FIG. 1, housing enclosure 3 has a reservoir plate 31 having a recessed portion defining a reservoir chamber 33 positioned radially outward of the assay chamber 5 and disposed below the valve chamber 23. Reservoir chamber 33 is in fluid communication with fluid drain 15. Fluid exiting the valve chamber 23 through the fluid drain 15 enters the reservoir chamber 33, as shown by arrow 21. Reservoir chamber 33 can be sized to accommodate any volume, preferably about 3 milliliters. As the volume of the reservoir chamber 33 is decreased the distance between the reservoir chamber 33 and the fluid drain 15 may also decrease. If the distance is such that fluid entry into the reservoir chamber is restricted, a fluid channel 16 may be included to provide a clear and unobstructed path for fluid exiting the fluid drain 15 to enter the reservoir chamber 33. Fluid channel 16 is disposed below the fluid drain 15 and is in fluid communication with the fluid drain 15 and the reservoir chamber 33. Fluid channel 16 has a first channel wall 18 disposed opposite to and substantially parallel with a second channel wall 20. Fluid channel 16 is substantially wider than fluid drain 15 and is substantially symmetrical with fluid drain 15.

It may be desirable to recover fluids used in an assay for subsequent analysis or reactions. Reservoir plate 31 may include fluid extraction means 35 in fluid communication with the reservoir chamber 33 and the exterior of the reservoir plate 31. Preferably, the fluid extraction means 35 is self sealing, for example, a diaphragm or a septum. Typically, a syringe or the like is inserted through the fluid extraction means 35 and fluid is withdrawn from the reservoir chamber 33.

FIG. 1 illustrates an alternative embodiment of the present invention. Air or gas 39 displaced by fluid 21 entering the reservoir chamber 33 from centrifugal force-activated valve 7a is vented to the exterior of housing enclosure 3 through a vapor vent 37 of centrifugal force-activated valve 7b. Vapor vent 37 is in fluid communication with the valve chamber 73 of centrifugal force-activated valve 7b. Rotation 6 of the housing enclosure 3 above the rotational speed necessary to actuate valve 7b from the stationary position to the actuated position, forces the actuator 77 to disengage from the valve seat 75. Air or gas 39 enters the valve chamber 73 through the fluid drain 78 and exits the valve chamber 73 through the valve seat 75 and enters the vapor vent 37. Centrifugal force-activated valve 7a is in fluid communication with the assay chamber 5. Fluid 21 entering fluid drain 15 of valve 7a, displaces air or gas 39 in the reservoir chamber 33. Valve 7b is not in fluid communication with the assay chamber 5. However, the reservoir chamber 33 is common to both valve 7a and valve 7b; therefore, fluid entering the reservoir chamber 33 from centrifugal force-activated valve 7a displaces air or gas 39 through centrifugal force-activated valve 7b.

Figure 6:
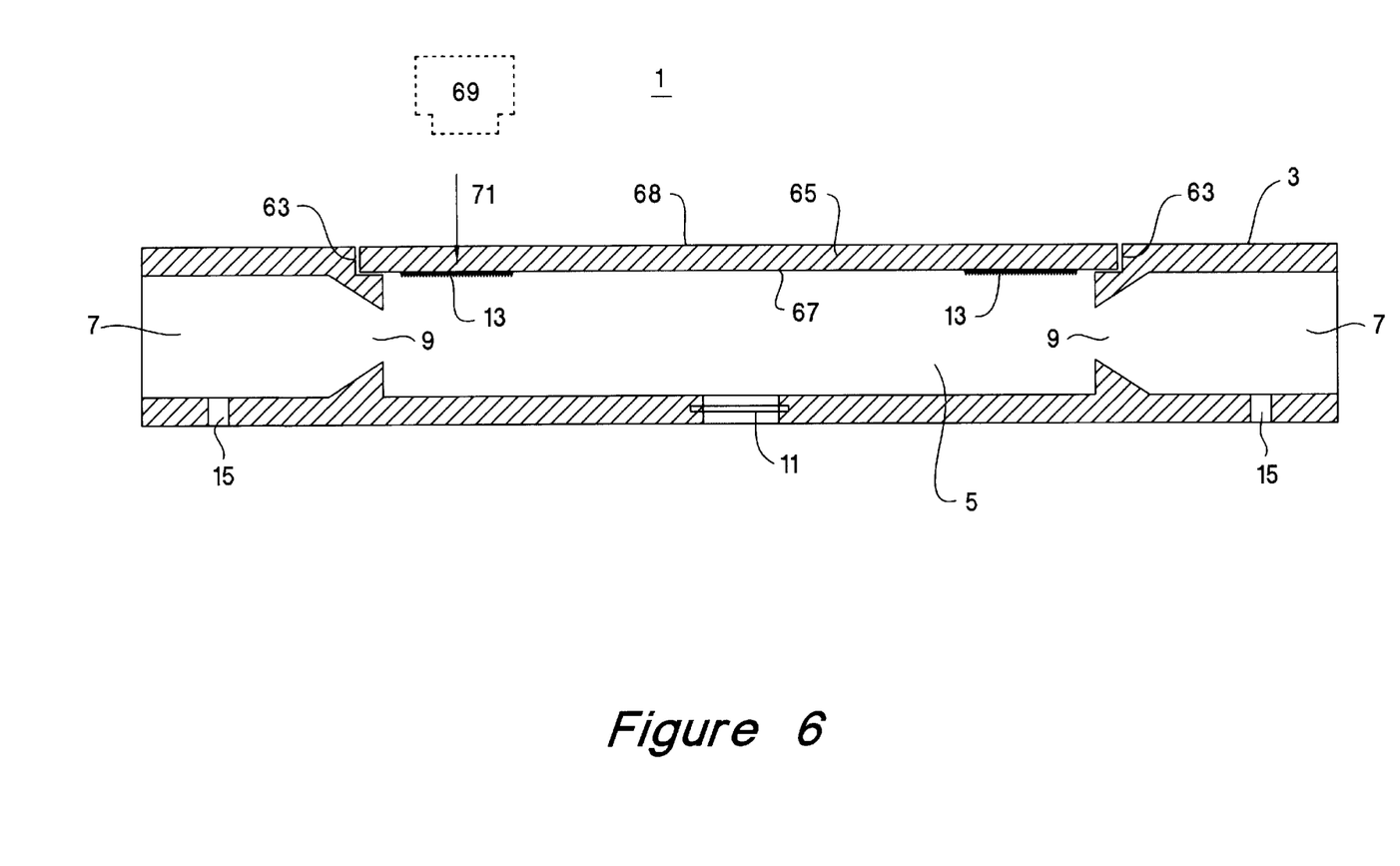
FIG. 6 is a cross section of an analytical device having a substrate disposed in the housing enclosure according to the present invention.

In a most preferred embodiment, the housing enclosure 3 has a portion defining an opening 63, as shown in FIG. 6. The opening 63 is positioned over the assay chamber. An analytical substrate 65 having an inner surface 67 and an outer surface 68 is disposed in the opening 63. The inner surface 67 is positioned above and in opposing relation to the assay chamber 5 and is in fluid communication with the assay chamber 5. An active surface 13 may be positioned on the inner surface 67 of the analytical substrate 65. Additionally, the analytical substrate 65 can be made transparent to optical detection means 69. The optical detection means 69 is external to the analytical device 1. The optical detection means 69, scans through the analytical substrate 65 to assay the active surface 13, as shown by arrow 71. Suitable materials for the analytical substrate 65 include glass, plastics, fused silica, and quartz. The analytical substrate 65 can be secured in the opening 63 using glue, adhesives, a weld, fasteners, or the like. Preferably, the active surface 13 is positioned at a radially outward portion of the inner surface 67, so that fluid directed radially outward by rotation 6 of the housing enclosure 3 will be urged into contact with the active surface 13.

In alternative preferred embodiments, the active surface 13 includes biochemical, chemical, or biological moieties. The active surface 13 can be disposed on the surface of a structure attached to the inner surface 67 of the analytical substrate 65, for example, balls, beads, or other structure that can be fixedly attached to the inner surface 67. The active surface 13 may comprise an array or other orderly structure of biomolecular probes. The biomolecular probes can be DNA, DNA fragments RNA, RNA fragments, reagents, protein, protein fragments, lipids, and lipid fragments. A dye, label, tag, or reagent may be attached or dried onto-to the active surface. Alternatively, fluid introduced into the assay chamber 5 may contain a dye, label, tag, or reagent. Preferably, the active surface 13 is disposed at a radially outward position on the assay chamber 5 or the analytical substrate 65. Rotation 6 of the analytical device 1, generates a radially outward flow of the fluid, bringing the fluid into contact with the active surface 13.

Additionally, the active surface 13 can be disposed on the surface of a structure that is not attached to the analytical substrate 65 or to the interior surface of the assay chamber 5. For example, the active surface 13 can be disposed on balls or beads loosely contained in the assay chamber 5. Further, after the conclusion of a reaction, the balls or beads can be extracted from fluid remaining in the valve chamber 23 via the fluid extraction means 49 in valve chamber cap 42 as illustrated in FIG. 2b or from fluid captured in the reservoir chamber 33 via the fluid extraction means 35 in the reservoir plate 31 as illustrated in FIG. 1.

The best mode for making the analytical device 1 is to injection mold the housing enclosure 3, preferably from plastic. The bias means 29 is a coil spring and the actuator 27 is a stainless steel ball. Preferentially, an o-ring is positioned on the valve seat 25 between the actuator 27 and the valve seat 25, to supply compliance. The coil spring holds the stainless steel ball against the o-ring of the valve seat 25.

In a preferred embodiment of a method according to the present invention, a fluid sample may be introduced into the assay chamber 5 via fluid introducing means 11. The analytical device 1 is spun at a first rotational speed to generate a radially outward flow of the sample, whereby the fluid reacts with the active surface 13. The first rotational speed is below the threshold rotational speed necessary to actuate the centrifugal force-activated valve 7, from the stationary closed state to the open actuated state. The closed valve 7 prevents the sample from exiting the assay chamber 5 through the valve 7. Spinning at the first rotational speed continues until a predetermined reaction time has passed or the reaction has reached a is desired state of completion. After spinning at the first rotational speed, the analytical device 1 is then spun at a second rotational speed greater than the first rotational speed. The second rotational speed exceeds the threshold rotational speed necessary to actuate the valve to the open actuated state. The centrifugal force-activated valve 7 opens and fluid exits the assay chamber 5 through the valve 7. The introducing step, the first rotational speed step, and the second rotational speed step may be repeated as necessary to complete the reaction.

In an alternate embodiment, after spinning the analytical device 1 at the second rotational speed, a wash fluid may be introduced into the assay chamber 5 via fluid introducing means 11. The analytical device 1 is spun at a first rotational speed to distribute the wash fluid. The wash fluid removes un-reacted sample from the active surface 13 and the assay chamber 5. The analytical device 1 is then spun at the second rotational speed to remove the wash fluid from the assay chamber 5. The introducing step, the first rotational speed step, and the second rotational speed step may be repeated as necessary to ensure complete washing of the active surface 13 and the assay chamber 5.

In another embodiment, the analytical device 1 is spun at the second rotational speed to remove any sample remaining in the assay chamber 5. The active surface 13 is assayed by scanning the active surface 13 with optical detection means 69. The optical detection means are external to the analytical device 1.

In the most preferred embodiment of a method according to the present invention, the analytical device 1 includes an analytical substrate 65 having an active surface 13 disposed on a radially outward portion. A fluid sample is introduced into the assay chamber 5 via fluid introducing means 11. The analytical device 1 is agitated to mix the sample and to generate a radially outward flow of the sample, whereby the sample reacts with the active surface 13. The agitation can be accomplished, for example, by reversing the direction of rotation 6 of the analytical device 1 multiple times. Mixing continues until a predetermined reaction time has passed or the reaction has reached a desired state of completion. The analytical device 1, is then spun at the second rotational speed to empty the sample from the assay chamber 5. The introducing step, the mixing step, and the second rotational speed step may be repeated as necessary to complete the reaction.

In an alternate embodiment, after spinning the analytical device 1 at the second rotational speed, a wash fluid may be introduced into the assay chamber 5 via fluid introducing means 11. The analytical device 1 is spun at a first rotational speed to generate a radially outward flow of the wash fluid. The wash fluid removes un-reacted sample from the active surface 13, the analytical substrate 65, and the assay chamber 5. The analytical device 1 is then spun at the second rotational speed to empty the wash fluid from the assay chamber 5. The introducing step, the first rotational speed step, and the second rotational speed step may be repeated as necessary to ensure complete washing of the active surface 13, the analytical substrate 65, and the assay chamber 5.

In another embodiment, the housing enclosure 3 has a reservoir plate 31 positioned radially outward of the assay chamber 5 and positioned below the centrifugal force-activated valve 7a. Reservoir plate 31 includes a reservoir chamber 33. The analytical device 1 is spun at the second rotational speed to remove fluid from the assay chamber 5. Centrifugal force-activated valve 7a, opens and fluid exits the assay chamber, enters the valve, and is stored in the reservoir chamber 33. Optionally, fluid in the reservoir chamber 33 may be removed via fluid extraction means 35. A syringe or the like may be used to withdraw fluid from the reservoir chamber for further analysis or other use.

In another embodiment, the analytical device 1 is spun at the second rotational speed to remove any sample remaining in the assay chamber 5. The analytical substrate 65 is transparent to optical detection means 69. The active surface 13 is assayed by scanning the active surface 13 through a transparent portion of the analytical substrate 65 via the optical detection means 69. The optical detection means are external to the analytical device 1.

Although several specific embodiments of the invention have been described and illustrated, the invention is not limited to the specific forms or arrangements of parts so described and illustrated. The invention is only limited by the claims.

What is claimed is:

1. An analytical device for controlling reactions, comprising:

a housing enclosure defining an assay chamber and a fluid discharge port positioned radially outward from the assay chamber and in fluid communication with the assay chamber, the housing enclosure adapted for rotation about an axis;

means for introducing fluid into the assay chamber; and a centrifugally-operated valve in fluid communication with the fluid discharge port, the valve repetitively operable between a stationary position and an actuated position, the valve operative to transition from the stationary position to the actuated position when a centrifugal force generated by rotating the housing enclosure exceeds a predetermined limit, and to transition from the actuated position to the stationary position when the centrifugal force does not exceed the predetermined limit.

2. The device of claim 1, wherein the means for introducing is self sealing.

3. The device of claim 2, wherein the means for introducing comprises a septum.

4. The device of claim 1, further comprising an active surface disposed in the assay chamber.

5. The device of claim 4, wherein the active surface is disposed on balls positioned in the assay chamber.

6. The device of claim 4, wherein the active surface is disposed on beads positioned in the assay chamber.

7. The device of claim 4, wherein the active surface comprises biomolecular probes.

8. The device of claim 7, wherein the biomolecular probes are selected from the group consisting of DNA, DNA fragments, RNA, RNA fragments, reagents, protein, protein fragments, lipids, and lipid fragments.

9. The device of claim 1, wherein the valve comprises:
- a valve chamber in fluid communication with the fluid discharge port;
- an actuator movably disposed in the valve chamber;
- a valve seat disposed between the valve chamber and the fluid discharge port, the valve seat in fluid communication with the valve chamber and the fluid discharge port; and
- bias means for producing a counteracting force to urge the actuator to a stationary position relative to the valve seat, the bias means disposed in the valve chamber and positioned radially outward from the actuator, the actuator operative to move radially outward from the stationary position to an actuated position when the housing enclosure is rotated and the centrifugal force acting on the actuator exceeds the counteracting force of the bias means, and to move radially inward from the actuated position to the stationary position when the centrifugal force acting on the actuator does not exceed the counteracting force of the bias means.

10. The device of claim 9, further comprising a compliant material conformally disposed on the valve seat, the compliant material operative to form a tight seal between the actuator and the valve seat when the actuator is forcefully engaged with the valve seat.

11. The device of claim 9, wherein the bias means is selected from the group consisting of a compression spring, a compressible material, a leaf spring, a coil spring, and a diaphragm.

12. The device of claim 9, wherein the actuator is selected from the group consisting of a steel ball, a machined shape, and a molded shape.

13. The device of claim 12, further comprising an elastomeric material disposed on the actuator, the elastomeric material operative to form a tight seal between the actuator and the valve seat when the actuator is forcefully engaged with the valve seat.

14. The device of claim 9, wherein the actuator is positioned radially outward from the valve seat and the bias means is operative to urge the actuator into engagement with the valve seat, whereby the valve is normally closed, thereby preventing fluid communication between, the valve chamber and the fluid discharge port when the actuator is in the stationary position.

15. The device of claim 9, wherein the actuator is positioned radially inward from the valve seat and the bias means is operative to disengage the actuator from the valve seat, whereby the valve is normally open, thereby allowing fluid communication between the valve chamber and the fluid discharge port when the actuator is in the stationary position.

16. The device of claim 1, further comprising an analytical substrate disposed in an opening in the housing enclosure, the analytical substrate having an inner surface in fluid communication with the assay chamber.

17. The device of claim 16, further comprising an active surface disposed on the inner surface of the analytical substrate.

18. The device of claim 17, wherein the analytical substrate is transparent, whereby the active surface can be scanned through the analytical substrate to allow an assay of the active surface.

19. The device of claim 17, wherein the active surface is disposed on balls positioned on the inner surface of the analytical substrate.

20. The device of claim 17, wherein the active surface is disposed on beads positioned on the inner surface of the analytical substrate.

21. The device of claim 17, wherein the active surface comprises biomolecular probes.

22. The device of claim 21, wherein the biomolecular probes are selected from the group consisting of DNA, DNA fragments, RNA, RNA fragments, reagents, protein, protein fragments, lipids, and lipid fragments.

23. The device of claim 1, wherein the housing enclosure defines a single assay chamber.

* * * * *